United States Patent [19]

Bousquet et al.

[11] 4,282,140
[45] Aug. 4, 1981

[54] ACRYLIC CEMENT APPLICABLE IN BONE SURGERY AND IN STOMATOLOGY

[75] Inventors: Gilles Bousquet, Saint Etienne; Jean-Bernard Egraz, Ecully; Andre Rambert, Lyons; Georges Ravet, Saint Genis les Ollieres, all of France

[73] Assignee: Societe d'Exploitation des Procedes Coatex, Caluire, France

[21] Appl. No.: 13,891

[22] Filed: Feb. 22, 1979

[30] Foreign Application Priority Data

Feb. 22, 1978 [FR] France ................................ 78 06377

[51] Int. Cl.$^3$ ........................ C08F 8/00; C08L 33/06; C08F 265/04
[52] U.S. Cl. ............................... 260/42.52; 260/42.17; 525/166; 525/179; 525/193; 525/228; 525/309
[58] Field of Search ....................... 525/309, 193, 228; 260/42.52, 42.17

[56] References Cited

U.S. PATENT DOCUMENTS

| | | | |
|---|---|---|---|
| 2,468,094 | 4/1949 | Marks | 260/885 |
| 2,798,060 | 7/1957 | Rawitzer et al. | 525/309 |
| 3,154,600 | 10/1964 | Munn | 525/309 |

Primary Examiner—Carman J. Seccuro
Attorney, Agent, or Firm—McDougall, Hersh & Scott

[57] ABSTRACT

New medical self-polymerizable sealing cement with an acrylic polymer and/or copolymer base, applicable for prosthetic implants, which is obtained by mixing a liquid phase and a solid phase. The liquid phase, being viscous, forms a collodion of an acrylic polymer and/or copolymer in at least one monomer, while the solid phase is composed of an acrylic polymer and/or copolymer possibly containing a mineral load.

The new cement is not dangerous for the patient, due to an absence of monomer exudation and due to a polymerization temperature which is always lower than the mobilization temperature of human fat.

9 Claims, No Drawings

ACRYLIC CEMENT APPLICABLE IN BONE SURGERY AND IN STOMATOLOGY

The present invention pertains to a new auto-polymerizable cement belonging to the acrylic group, designed to ensure the sealing of intra-bone prostheses; the sealing cement is composed of a viscous liquid phase made up of an acrylic polymer and/or copolymer collodion and a solid phase made up of said polymer and/or copolymer with possibly a mineral load.

For many years now, medical science has created and developed multiple partial or total prostheses, such as those intended for the knee, elbow, shoulder, hip, etc., designed to be substitutes for the joints of the human skeleton which have failed due to sickness, ageing or other accidental causes.

However, due to difficulties in fitting the prosthesis to the bone, or due to the bad quality of the cortical-spongy bone, the implantation of such prostheses required sealing cements which could be tolerated by the human organism, easily manipulable during an operation, quickly installed "in situ", and which exhibited good mechanical properties after hardening.

It is for these reasons that, for a long time, surgeons and chemists have tried to develop polymer material base sealing cements which man could tolerate and which would last in such a way that unsealing and rejections would occur as infrequently as possible. This is why, in bone surgery, the surgeon and the dental surgeon have been led to use sealing cements composed of a liquid phase made up of a monomer, methyl methacrylate, and a solid phase principally composed of polymethyl-methacrylate. Specialized literature teaches that both phases thusly defined were sterilized, preserved separately in ampoules or envelops, and then mixed exactly when used. At the end of mixing, the material obtained had the consistency of an oily paste usable in this form, or else as a mass which could be kneaded by hand, after an adequate rest time, so that polymerization would begin.

Introduced then into the bone cavity, this material, either oily paste or kneadable mass, finished polymerizing "in situ", giving a hard, resistant mass which provided cohesion between the prosthesis and the skeleton receiver bone.

The same literature also tells the sources of the components of both the solid and liquid phases of the acrylic cements.

First, the liquid phase was composed of a monomer, such as methyl methacrylate to which could be added certain adjuvants, such as polymerization accelerators, colorants.

Then, the solid phase was composed, for the most part, of a polymer in the form of a white powder, such as polymethyl methacrylate, and certain adjuvants present in small quantities such as, for example, a root polymerization initiator, possibly an x-rays sensitive contrast agent, biocide agents to limit risks of infection, etc.

The relative quantities of the liquid and solid phases, brought together during the preparation of the cement, were approximately 1:2 in ponderal weight.

Because of their reputation, it seemed undeniable that these cements constituted the beginning of notable progress in the field of prosthetic implants, for they proved that they were tolerated by the human organism and practical because they set quickly in not more than fourteen minutes. Yet their qualities over a period of time were not able to be anticipated.

However, with usage, it was seen that these sealing cements displayed some major disadvantages, sufficiently damaging to endanger the life of the patient or cause irreversible, significant local lesions when rejected by the receiver bone and surrounding tissues.

In the first place, polymerization of such acrylic cements is very exothermic, and when it occurs "in situ", it causes, for a short period of 4–5 minutes, a significant, localized increase in temperature which can reach a threshold of 100° C. Although the quantity of cement is limited in units, this temperature increase, as soon as approximately 65° C. is reached, is sufficient to cause the melting and dissolution of human fat and the coagulation of proteins.

Yet, certain medical publications have raised the disturbing idea that an increase in this temperature beyond 100° C. presented no drawback because it was compensated by the lower temperature of the receiver medium and consequently, that it did not reach the above-mentioned critical temperatures.

More than that, liquid monomer, such as methyl methacrylate, is a powerful solvent of human fat, and this is even more so as the temperature of the medium increases, thereby facilitating its diffusion, and as it exudes from the cement during polymerization "in situ", it dissolves said fats, carrying them along as it flows through the blood stream of the patient.

Therefore, serious secondary effects were able to be noted when the prosthesis was implanted. These secondary effects show themselves still today in the rapid, significant fall of the patient's blood pressure, sometimes resulting in failure of the cardiac pump, heart failure and patient death. They also show themselves in fat embolisms, resulting from the presence of peripheral fats carried in the blood to the lungs, and which present difficulties for the surgeon and the resuscitator.

In addition to the dangers cited above, there are other, certainly less important drawbacks, the manifestations of which result naturally from the great exothermicity of the reaction. In numerous cases, it was noted that the great exothermicity of the polymerization reaction caused large lesions by burns to the surrounding tissues as well as necrosis of the surface bone layers in contact with the cement.

It was noted by several authorities that exothermicity indeed caused a bone burn which could evolve in one of three directions: the first corresponding to a surface, reversible burn, healing within three months after the operation and leaving a stable prosthetic implant; the second being a deeper burn with a scaring time estimated at more than six months, during which time the patient can catch an intercurrent infection; and the third being profound and irreversible necrosis, causing the bone to die and the consequences of which, possibly occurring four to five years afterwards, are well known to bone surgeons. Depending on the evolutive stages of the burn, the bonding qualities of the sealing cement to the bone vary to a considerable extent. Consequently, there are dangers that the prosthesis will unseal, making new surgery necessary.

Very conscious of the risks from exothermicity of the polymerization reaction being too great, and having witnessed accidental deaths at the time of prosthesis implant surgery, but equally aware that polymethyl methacrylate sealing cements provide, among other things, great inocuity with respect to the human organism, the sciences of surgery and chemistry have tried to improve these cements sufficiently in order that their use not be limited or stopped by the above-mentioned effects.

This is why there has been proposed an improved polymethyl-methacrylate base sealing cement composed of a liquid phase consisting of an aqueous emulsion of methyl methacrylate and a solid phase consisting of polymethyl methacrylate. Since, during polymerization "in situ", the quantity of heat freed from the mixture of both phases depends on the quantity of monomer present, it seemed possible to reduce the reaction temperature increase by having a part of the calories which are freed during the reaction absorbed by the water present in rather large quantity in the monomer.

The scientist considered this cement a palliative but not a real solution to the major drawbacks cited above.

Because, if the practitioner noted that such a product permitted an appreciable reduction in the reaction temperature and lessened the risks of burns to the surrounding tissues and necrosis of the receiver bone, he also noted that while some of the above-mentioned drawbacks persisted, others, although minor in character, appeared.

This is why, for example, that this cement, during its usage, appeared too fluid to be handled easily, this great fluidity encouraging its flow to the inside of the receiver bone well beyond the area involved, and making it practically necessary to use a much larger quantity of cement than normal to ensure setting of the prosthesis. Therefore, this flow even becomes harmful.

Moreover, in the field of biochemistry, it is well known that the presence of water favors the diffusion of an organic liquid in living tissues and this is even more so in the presence of an emulsive substance for lowering surface tension. During polymerization "in situ" of the above-mentioned sealing cement, its liquid phase being an emulsion of methyl methacrylate in water, heterogeneity of the reaction occurs by rupture of the emulsion with the freeing of water and methyl methacrylate (and this is a well known phenomenon in chemistry of polymerization in emulsions). Therefore, the presence of water especially promotes the flow of the monomer, which as we have said was particularly active in that it is a powerful solvent of human fat, through the blood stream of the patient, increasing such risks as significant drops in blood pressure, heart failure, fat embolisms, etc.

Although cements used for installing orthopedic or stomatological implants have been improved, these improvements were not sufficient so that the surgeon could operate without concern, i.e., without running the general, local risks mentioned above.

Consequently, it became imperative for the safety of the patient, that the cement used to seal bone implants be accepted by the human organism, that it be sufficiently pasty so as to be easily manageable by the practitioner, that its polymerization temperature "in situ" be lower than the mobilization temperature of human fat, and finally that the dangerous monomer be unable to enter the blood stream by preventing its diffusion during polymerization.

Pursuing his research in this field, the applicant has developed a new, self-polymerizable sealing cement, applicable for prosthetic implants, belonging to the acrylic group, and with which it is possible to practically eliminate the above-cited drawbacks.

The new, self-polymerizable sealing cement is characterized in that it is composed of a viscous liquid phase made up of a collodion of an acrylic polymer and/or copolymer in at least one monomer, and a solid phase made up of an acrylic polymer and/or copolymer with possibly a mineral load.

The viscous liquid phase, made up of a collodion, is composed of at least 65% by weight of an acrylic monomer and between 15% and 35% by weight of acrylic polymer and/or copolymer, but preferably between 25% and 35%.

Said viscous phase is obtained either by the dissolution at a low temperature of the polymer and/or copolymer no longer having free radicals in the monomer, or by partial polymerization of the monomer, carried out by stopping the reaction according to a known means, in such a way that a dry extract within the above-mentioned limits is obtained.

The monomer used in the preparation of the viscous liquid phase belongs to the group composed of acrylic and methacrylic esters such as, for example, acrylates and methacrylates of methyl, ethyl, propyl, butyl; these esters are chosen so as to have the lowest toxicity possible.

The polymer materials used in the preparation of the viscous liquid phase are, in general, an acrylic and/or methacrylic polymer or copolymer. But, it can also be a mixture of acrylic and/or methacrylic polymer and copolymer. Among the most commonly used materials, polymethacrylates of methyl, ethyl, propyl and butyl as well as their copolymers can be cited.

The viscous liquid phase forming a collodion may also contain classic adjuvants such as polymerization catalysts and cross-linking agents.

The polymerization catalysts are well known to the scientist and involve peroxides and mainly benzoyl peroxide, percarbonates to which are added tertiary amines such as, for example, NN' dimethylparatoluidine.

The cross-linking agents are also well known to the scientist and involve all products of organic origin capable of cross-linking two chains simultaneously and having at least two free double bonds. Such is the case, for example, of glycol ethylene dimethacrylate, trimethylolpropane diallylether, tetra allyloxyethane.

As it has already been stated, the cement according to the invention, in addition to the viscous liquid phase made up of a collodion, also consists of a solid phase formed of an acrylic polymer or copolymer or their mixtures, and possibly accompanied with a mineral load. This is generally polymethyl-methacrylate in the form of powder or fine granules, the granulometry of which is not critical and may easily reach 500 microns. The applicants have noted in effect, that said granulometry should be chosen with respect to the subsequent manageability of the cement. Furthermore, the applicants have noted that in certain cases, the addition of a mineral load, such as, for example, a load composed of alumina, is advantageous.

Depending on the mechanical qualities desired, the solid phase may also contain various adjuvants among which can be cited cross-linking agents, polymerization catalysts, and also Xray sensitive contrast agents, biocide agents, colorants, etc.

Generally speaking, the sealing cement according to the invention is obtained by mixing the viscous liquid phase made up of a collodion with the solid phase, in ratios between 1:2.5 and 1:0.5 by ponderal weight, but the preferred ratio is 1:1.5.

In practice, the two phases are preserved separately in sterile containers in the above-mentioned ponderal proportions; when used, they are mixed by stirring so as to obtain a homogeneous paste easily manageable by the practitioner.

Setting is usually finished within fifteen minutes, giving the surgeon time to place the cement in the given cavity, being understood that this length of time depends on ambiant temperature.

Polymerization of the sealing cement according to the invention, once it begins, occurs with relatively low heating, which never exceeds the mobilization temperature of human fat, i.e., approximately 65° C.

For certain uses, and in order to improve the mechanical properties of the sealing cement even more, it can be valuable to add a small quantity of short fibers such as, for example, carbon fibers, acrylic fibers, polyamide fibers, polyester fibers, etc.

The sealing cement according to the invention provides particularly remarkable and valuable qualities for both the physician and his patient.

First, this new combination of a viscous liquid phase composed of a collodion and a solid phase dispersed in this collodion during surgery prevents the dangerous methyl methacrylate monomer from exuding into the body of the patient, because of the very small quantity of this solvent used and because of its retention in the collodion. The notable reduction of the diffusion of the monomer therefore greatly limits known risks.

Furthermore, such a cement provides another advantage, especially valuable and advantageous where the subsequent good holding properties of the prosthesis is concerned; since the viscous phase is made up of the collodion, it causes a lowering of the temperature increase by controlling polymerization speed.

Thus, the maximum temperature does not exceed 65° C., which is always considerably lower than the temperature noted for commonly used cements. Therefore, it can be considered that burns to living tissues and necrosis of the receiver bone are reduced, hopefully allowing for bone recovery and good setting of the prosthesis, ensuring better safety and longevity.

EXAMPLES 1-9

A mass of 67 g of sealing cement was produced according to the invention by mixing 27 g of polymer collodion with 40 g of solid polymer, in powder form. The collodion was obtained in the following manner:

in examples 1-5, dissolution of 30% of polymethyl methacrylate in 70 % of methyl methacrylate monomer at approximately 20° C. and under constant stirring of the medium, yielding a viscous substance of 500 centipoises at 20° C.

in examples 6-8, dissolution of polymethyl-methacrylate in 70% of monomer made up of an 80/20 mixture of methyl and butyl methacrylate yielding a viscous substance of 300 centipoises at 20° C.

in example 9, the solid phase also contained a mineral load composed of alumina.

The cement was obtained by mixing and polymerizing both phases together according to the ponderal proportions given in the following table, as well as the polymerization catalysts, cross-linking agents and x-rays opacification agents.

The exothermicity of the polymerization reaction has been carefully observed by measuring initial and maximum temperatures at the core of the reaction medium.

Finally, the polymerization times were also measured and are given in minutes.

TABLE 1

| | Examples N.<br>Composition in percent by weight | 1 % | 2 % | 3 % | 4 % | 5 % | 6 % | 7 % | 8 % | 9 % |
|---|---|---|---|---|---|---|---|---|---|---|
| VISQUEOUS PHASE forming collodion | 30% polymethyl methacrylate in methyl methacrylate and butyl methacrylate 500 cP 20° C. 80/20 | | | | | | 39 | 39.5 | 38.5 | |
| | 30% polymethylmethacrylate dissolved in 70% methylmethacrylate - 300 cP at 20° C. | 40 | 40 | 38 | 37 | 40 | | | | 38.5 |
| | NN' dimethylparatoluidine | 0.6 | 0.6 | 0.6 | 0.6 | 0.6 | 0.6 | 0.6 | 0.6 | 0.6 |
| | Zirconium dioxide | | | 6 | | | | | | |
| | Barium sulfate | | | | 4.5 | | | | | |
| SOLID PHASE | polymethyl methacrylate <500μ | 59 | | 56 | | | | 58 | 58 | 29 |
| | Butyl and methyl methacrylate copolymer <500μ | | 59 | | 57.6 | 59 | 58 | | | |
| | Benzoyl peroxide | 0.3 | 0.3 | 0.3 | 0.3 | 0.3 | 0.4 | 0.4 | 0.4 | 0.4 |
| | Trimethylolpropanediallyle ether | | | | | 1 | 2 | | | |
| | Diallyle maleate | | | | | | 1.5 | | | |
| | Bis acrylamide methylene | | | | | | | | 2.5 | |
| | Mineral load: alumina | | | | | | | | | 29 |
| CEMENT | Exothermicity measured by difference between: | | | | | | | | | |
| | initial temperature °C. | 25 | 25 | 25 | 25 | 25 | 25 | 25 | 25 | 25 |
| | maximum temperature recorded °C. | 54 | 53 | 51 | 52 | 52 | 49 | 50 | 53 | 48 |
| | time in minutes end of reaction | 15 | 14 | 13 | 14 | 14 | 15 | 13 | 15 | 16 |

For comparison purposes, five types of cements A,B,C,D and E belonging to prior art and currently used for the sealing of prostheses were tested. Their compositions, expressed in percent by weight, as well as their exothermicity and setting times, are given in table 2 below:

| Current cements<br>Formula in % by weight | A % | B % | C % | D % | E % |
|---|---|---|---|---|---|
| Polymethyl methacrylate 200μ | | 65.4 | 57.6 | 69 | 63 |
| Polymethyl methacrylate 70 polymethylacrylate 30 200μ | 64 | | | | |
| Benzoyl peroxide | 0.4 | 0.32 | 0.33 | 0.25 | 0.3 |
| Methyl methacrylate | 28 | 29 | 32 | 30.7 | 35.4 |
| NN' Dimethylparatoluidine | 0.7 | 0.72 | 0.6 | 0.6 | 0.6 |
| Zirconium dioxide | 7 | | 10 | | |
| Barium sulfate | | 4.5 | | | |
| Exothermicity | | | | | |
| initial temperature °C. | 25 | 25 | 25 | 25 | 25 |

-continued

| Current cements Formula in % by weight | A % | B % | C % | D % | E % |
|---|---|---|---|---|---|
| max. temperature recorded °C. | 90 | 80 | 78 | 85 | 90 |
| Time in minutes end of reaction | 11 | 14 | 13 | 20 | 19 |

We claim:

1. The method of preparing an acrylic homopolymer and/or copolymer base self-polymerizable sealing cement, applicable for prosthetic implants, the purpose of which is the safety of the patient due to the absence of monomer exudation and due to a polymerization temperature which is always lower than the mobilization temperature of human fat, said cement being prepared by mixing a liquid phase and a solid phase in a weight ratio range of 1 to 0.5–2.5, in which the liquid phase is a collodion formed of an acrylic homopolymer and/or copolymer selected from the group consisting of polyalkylacrylate, polyalkylmethacrylate and copolymers consisting of alkylacrylates and/or alkylmethacrylates in which the alkyl group is methyl, ethyl, propyl or butyl in at least one acrylic monomer selected from the group consisting of alkylacrylate and alkylmethacrylate in which the alkyl group is methyl, ethyl, propyl or butyl consisting of at least 65% by weight of acrylic monomer and between 15% and 35% by weight of acrylic homopolymer and/or copolymer, and in which the solid phase is composed of an acrylic homopolymer and/or copolymer selected from the group consisting of polyalkylacrylate, polyalkylmethacrylate and copolymers consisting of alkylacrylates and/or alkylmethacrylates.

2. The method as claimed in claim 1, in which the collodion forming a viscous phase consists of at least 65% by weight of acrylic monomer and between 25% and 35% by weight of acrylic homopolymer and/or copolymer.

3. The method as claimed in claim 1, in which the collodion forming a viscous phase is obtained by dissolution at a low temperature of the homopolymer and/or copolymer in the monomer.

4. The method as claimed in claim 1, in which the collodion forming a viscous phase is obtained by partial polymerization of the monomer by voluntarily stopping the reaction.

5. The method as claimed in claim 1, in which the solid phase contains a mineral load.

6. The method as claimed in claim 1, in which the weight ratio of liquid phase to solid phase is about 1 to 1.5.

7. The method as claimed in claim 1, which includes fibers selected from the group consisting of carbon fibers, acrylic fibers, polyamide fibers and polyester fibers.

8. The method as claimed in claim 1 which includes a polymerization catalyst.

9. The method as claimed in claim 1 which includes a cross linking agent.

* * * * *